United States Patent [19]

Bahal

[11] 3,993,753

[45] Nov. 23, 1976

[54] ANHYDROUS AMPICILLIN STABILIZATION AND RESULTANT COMPOSITIONS

[75] Inventor: Surendra M. Bahal, Audubon, Pa.

[73] Assignee: American Home Products Corporation, New York, N.Y.

[22] Filed: Aug. 21, 1975

[21] Appl. No.: 606,386

Related U.S. Application Data

[63] Continuation-in-part of Ser. No. 500,242, Aug. 26, 1974, abandoned, which is a continuation-in-part of Ser. No. 44,548, June 8, 1970, Pat. No. 3,867,523.

[52] U.S. Cl................................. 424/176; 424/271
[51] Int. Cl.$^2$.................. A61K 31/00; A61K 47/00
[58] Field of Search............................ 424/176, 271

[56] References Cited
UNITED STATES PATENTS 3,317,389  5/1967  Granatek et al.................... 424/271
3,351,527  11/1967  Apat et al.......................... 424/175

OTHER PUBLICATIONS

Physician's Desk Reference, 22nd Ed. (1968), pp. 582–583.

Primary Examiner—V. D. Turner
Attorney, Agent, or Firm—Joseph Martin Weigman

[57] ABSTRACT

The formation of hydrates of anhydrous ampicillin in aqueous suspension may be retarded or entirely prevented for extended periods by (1) the addition of about 70 to 86% w/v of sucrose and (2) adjustment of the product pH to about 5.0 to 6.5. The invention is useful in extending the shelf life of aqueous dosage forms of anhydrous ampicillin.

4 Claims, No Drawings

ANHYDROUS AMPICILLIN STABILIZATION AND RESULTANT COMPOSITIONS

This application is a continuation-in-part of application Ser. No. 500,242 filed Aug. 26, 1974 and now abandoned which was a continuation-in-part of application Ser. No. 44,548 filed June 8, 1970 which issued as U.S. Pat. No. 3,867,523 on Feb. 18, 1975.

This invention relates to methods of stabilization of aqueous suspensions of anhydrous, hydrate-forming ampicillin and to the resulting compositions. The stabilized compositions may be stored under all required temperature conditions, and particularly at about 2° to 30° C., without substantial changes in the physical properties of the suspension due to the formation of hydrates. More particularly, the invention is directed to aqueous suspensions of anhydrous ampicillin stabilized at about 5° to 25° C. by the addition of sucrose and buffering to about pH 5 to 6.5.

Anhydrous ampicillin in the absence of water is stable for long periods of time. However, for use, anhydrous ampicillin is made up into aqueous suspensions. Such aqueous suspensions have a relatively short storage life even when kept under refrigeration. Thus a problem in the pharmaceutical field has been that after a pharmacist has prepared and dispensed an aqueous suspension of anhydrous ampicillin, the therapeutic effectiveness of the suspension may greatly diminish during a regimen of treatment. The decline in effectiveness occurs even though the patient keeps the aqueous suspension under refrigeration.

The problem results from (1) the chemical instability of aqueous ampicillin suspensions at higher temperatures and lower pHs and (2) the physical or thermodynamic instability of aqueous ampicillin suspensions at lower temperatures and higher pHs.

When aqueous suspensions of the anhydrous ampicillin are stored, especially at refrigerated temperatures, crystal growth occurs which is due to the formation of the thermodynamically more stable hydrated form.

It is known that certain chemical compounds such as ampicillin, exist both as the anhydrous and hydrated forms. When an aqueous suspension formulation of anhydrous ampicillin are stored, especially at refrigerated temperatures, it has a tendency to show crystal growth, either macroscopically or microscopically or both, and other associated physical changes in the product. These changes have been shown to be due to the formation of the thermodynamically more stable crystal forms, the hydrated forms. It has been shown that the hydrated forms of ampicillin are thermodynamically the more stable crystal forms at the normal storage temperature for pharmaceutical suspensions. This means that anhydrous ampicillin aqueous suspensions formulated according to the present practice in the art will tend to convert to the more stable hydrate forms below the transition temperature of ampicillin. The transition temperature is the temperature at which all forms are thermodynamically stable. The transition temperature is 42° C. for ampicillin [Poole and Bahal, J. Pharm. Sci., 67, 1945 (1968)]. Because the transition temperature is well above that of normal storage conditions for the products, the conversion to the hydrated forms will occur when the suspensions are stored at either room temperature, about 20°-25° C., or under refrigerated conditions, about 2°-15° C. However, the conversion occurs more rapidly at 2°-15° C., the most typical storage condition for ampicillin as a result of its relatively poor chemical stability at higher temperature.

Changes in the crystal forms of anhydrous ampicillin are undesirable because they will affect its solubility and resultant biological absorption, as measured by blood levels plus the physical properties of the pharmaceutical suspensions. The anhydrous form of ampicillin is the more desirable form because it gives higher blood levels than the hydrated forms. The shelf life of an anhydrous ampicillin suspension is about two to three weeks following reconstitution from the dry powder form in which it is marketed. It is during this period of shelf life that maintenance of the anhydrous form is essential. See, for instance, "Physicochemical Factors Influencing the Absorption of the Anhydrous and Trihydrate forms of Ampicillin", Poole et al., Current Therapeutic Research, 10, 292 (1968). The dry powders for reconstitution commonly contain numerous pharmaceutical additives such as colors, flavors, buffers, sweeteners, and the like, but according to the present practice in the art the level and type of additives do not prevent the conversion of anhydrous ampicillin to its hydrated forms.

It is an object of the present invention to provide methods for the stabilization of anhydrous ampicillin in aqueous suspensions.

It is a further object of the present invention to provide methods for retarding the conversion of anhydrous ampicillin to its hydrated forms.

It is a particular object of the present invention to provide methods for the improvement of shelf life of aqueous suspensions of anhydrous ampicillin.

It is still another object of the present invention to provide aqueous compositions containing anhydrous ampicillin which are stabilized against hydrate formation.

It is a further object of the present invention to prevent the crystal growth and conversion to hydrates in aqueous suspension formulations of anhydrous ampicillin.

It is a particular object of the present invention to provide stabilized dosage forms of aqueous suspensions of anhydrous ampicillin which will yield its inherent blood level and have improved physical stability throughout their shelf life.

It has been found that the conversion of hydrate-forming anhydrous ampicillin to the less desirable hydrated forms when in aqueous suspensions may be prevented (1) by the use of suitable concentrations of soluble solutes such as sucrose, dextrose, galactose, and sodium chloride and (2) by the adjustment of an aqueous suspension product pH to about 3.0 to 6.5, preferably 4.0–6.5 depending on the solute. Preferred concentrations for the solutes are: 70–86% w/v sucrose, 5–50% w/v dextrose (glucose), 5–>70% w/v galactose, and 1–30% w/v sodium chloride.

The mechanism by which levels of suitable soluble solutes prevent anhydrous ampicillin hydration is not completely understood, and without wishing to be bound by a theory of operation, the initial postulation is that the solutes lower the solubility of anhydrous ampicillin, and that the lower solubility stabilizes the suspension by virtue of the fact that the solubility of the anhydrous species approaches the lower solubility of the hydrated forms to a sufficient extent to increase the free energy required for conversion to the hydrates.

It has been found, however, that the concentrations of the solutes required to achieve the objects of the invention will vary depending on the particular solute used. It has been further found that dissolution of a solute in the concentrations and the types usually used in pharmaceutical products will not produce the desired result.

As previously discussed, the tendency of ampicillin to convert to the hydrated species is greater at lower temperatures, such as about 2°–15° C., than at higher temperature such as 20°–35° C. For this reason it has been found that the concentration of soluble solute required to prevent hydrate formation at lower temperatures is normally greater than the concentration required at higher temperatures.

In order to disclose more clearly the nature of the present invention, specific examples of the practice of the invention are hereinafter given. It should be understood, however, that this is done solely by way of example and is intended neither to delineate the scope of the invention nor limit the ambit of the appended claims.

EXAMPLE 1

This example illustrates the use of a high level of solute to prevent the conversion of anhydrous ampicillin to the hydrated form in aqueous formulations.

A dry powder was prepared from each of the following recipes:

| Ingredient | Control | A. | B. | C. |
|---|---|---|---|---|
| Anhydrous Ampicillin | 2.00 Gm. | 2.00 Gm. | 2.00 Gm. | 2.00 Gm. |
| Sodium Benzoate | 0.40 Gm. | 0.40 Gm. | 0.40 Gm. | 0.40 Gm. |
| Sodium Citrate | 0.16 Gm. | 0.16 Gm. | 0.16 Gm. | 0.16 Gm. |
| Propylparaben | 0.01 Gm. | 0.01 Gm. | 0.01 Gm. | 0.01 Gm. |
| Methylparaben | 0.09 Gm. | 0.09 Gm. | 0.09 Gm. | 0.09 Gm. |
| Sucrose | — | 24.00 Gm. | 40.00 Gm. | 64.00 Gm. |
| Sucrose Concentration | (0% w/v) | (30% w/v) | (50% w/v) | (80% w/v) |

The following concentration ranges of solutes have been found effective at the temperatures indicated at a pH of between 5 and 6.5. The concentration ranges are given in terms of percent weight per volume of solute (% w/v) where > means "greater than" and < means "less than":

| | 5° C | | 25° C | |
|---|---|---|---|---|
| | minimum | preferred | minimum | preferred |
| sucrose | | 70 | >80 | 30* | 50** | >60 |
| dextrose | 50* | 10** | >50 | 15* | 5** | 20 |
| galactose | >70* | 10** | >70 | 15* | 5** | 20 |
| sodium chloride | | 20 | >25 | <5 | <5 |

*at pH 5.0
**at pH 6.5

The minimum amounts are effective with ampicillin batches which show least tendency for conversion under the conditions described above.

More sodium citrate or citric acid was added to adjust the pH to desired value.

The ingredients were mixed with water to make 80 milliliters (ml.) of the final suspension. The resulting suspensions had a concentration of 2.5% w/v of anhydrous ampicillin.

One group of samples was stored at room temperature (25° C ± 2° C.) and a second group of samples is stored under refrigerated conditions at a temperature of 5° C ± 2° C. The samples were viewed microscopically initially and at different intervals for up to two weeks. Any hydrate formation was noted by the appearance of long needles under the microscope which is characteristic of hydrate formation with ampicillin. The Differential Thermal Analysis Method (DTA) was used as a test for the presence of hydrated ampicillin. Periodic DTA were carried out using the Dupont Model 900 DTA apparatus to confirm microscopic results. The limit of detection was 10 percent hydrates in these and other experiments. The results are shown in Tables I-A and I-B.

TABLE I-A

Effect of Sucrose at pH 6.5

| Sample | Storage Temp. ° C | Initial Physical | Initial Microscopic | After 3 Days Physical | After 3 Days Microscopic | After 3 Days DTA | After 7 Days Physical | After 7 Days Microscopic | After 14 Days Physical | After 14 Days Microscopic |
|---|---|---|---|---|---|---|---|---|---|---|
| Control | 25 | H.S. | No needles | Growth | N.L.G. | — | N.L.G. | N.L.G. | N.L.G. | N.L.G. |
| A | 25 | H.S. | N.N. | N.C. | Large number > of needles | 20% | N.L.G. | N.L.G. | N.L.G. | N.L.G. |
| B | 25 | H.S. | N.N. | N.C. | N.C. | — | N.C. | N.C. | N.C. | N.C. |
| C | 25 | H.S. | N.N. | N.C. | N.C. | — | N.C. | N.C. | N.C. | N.C. |
| Control | 5 | H.S. | N.N. | Growth | N.L.G. | — | N.L.G. | N.L.G. | N.L.G. | N.L.G. |
| A | 5 | H.S. | N.N. | Growth | N.L.G. | — | N.L.G. | N.L.G. | N.L.G. | N.L.G. |
| B | 5 | H.S. | N.N. | Growth | N.L.G. | — | N.L.G. | N.L.G. | N.L.G. | N.L.G. |
| C | 5 | H.S. | N.N. | N.C. | N.C. | — | N.C. | N.C. | N.C. | Some needles (none at pH 6.2) |

H.S. - Homogeneous suspension
N.N. - No needles
N.L.G. - Needle like growth (almost complete conversion to needles)
N.C. - No change
N.T. - Not tested
Growth - Macroscopic growth as needles

TABLE I-B

| | | Effect of Sucrose at pH 5.0 | | | | | | | |
|---|---|---|---|---|---|---|---|---|---|
| | Storage | Initial | | After 3 Days | | After 7 Days | | After 14 Days | |
| Sample | Temp. °C | Physical | Microscopic | Physical | Microscopic | Physical | Microscopic | Physical | Microscopic |
| Control | 25 | H.S. | N.N. | Growth | N.L.G. | N.T. | N.T. | N.T. | N.T. |
| A | 25 | H.S. | N.N. | N.C. | Some needles | N.C. | Some needles | N.C. | Some needles |
| B | 25 | H.S. | N.N. | N.C. | N.C. | N.C. | N.C. | N.C. | N.C. |
| C | 25 | H.S. | N.N. | N.C. | N.C. | N.C. | N.C. | N.C. | N.C. |
| Control | 5 | H.S. | N.N. | Growth | N.L.G. | N.T. | N.T. | N.T. | N.T. |
| A | 5 | H.S. | N.N. | Growth | N.L.G. | N.T. | N.T. | N.T. | N.T. |
| B | 5 | H.S. | N.N. | Growth | N.L.G. | N.T. | N.T. | N.T. | N.T. |
| C | 5 | H.S. | N.N. | N.C. | N.C. | N.C. | N.C. | N.C. | N.C. |

As illustrated in Tables I-A and I-B, the preparations do not show, physically or microscopically, any crystal growth or the presence of the hydrated antibiotic under either room temperature or refrigerated storage conditions over a two week period where high amounts of sucrose are used. In the control which used no sucrose and the sample containing 30–50% w/v of sucrose, crystal growth is observed both physically nd microscopically under refrigerated storage. The Differential Thermal Analysis also shows excessive amounts of the hydrates with 30% sucrose sample stored at 25° at pH 6.5. No such changes occurred in the high sucrose (80%) formulations.

EXAMPLE 2

Table II

| | | Ampicillin Concentration: 5% w/v (250 mg./5 ml.) | | | | | | | |
|---|---|---|---|---|---|---|---|---|---|
| Sucrose Conc., % w/v | Storage Temp. °C | Initial | | After 3 Days | | After 7 Days | | After 14 Days | |
| | | Physical | Microscopic | Physical | Microscopic | Physical | Microscopic | Physical | Microscopic |
| None (Control) | 5 | H.S. | N.N. | Growth | N.L.G. | N.T. | N.T. | N.T. | N.T. |
| | 25 | H.S. | N.N. | Growth | N.L.G. | N.T. | N.T. | N.T. | N.T. |
| 50 | 5 | H.S. | N.N. | Growth | N.L.G. | N.T. | N.T. | N.T. | N.T. |
| | 25 | H.S. | N.N. | N.C. | N.C. | N.C. | N.C. | N.C. | N.C. |
| 60 | 5 | H.S. | N.N. | Some Growth | N.L.G. | Growth | N.L.G. | N.T. | N.T. |
| | 25 | H.S. | N.N. | N.C. | N.C. | N.C. | N.C. | N.C. | N.C. |
| 70 | 5 | H.S. | N.N. | S.G. | F.N. | S.G. | F.N. | S.G. | F.N. |
| | 25 | H.S. | N.N. | N.C. | N.C. | N.C. | N.C. | N.C. | N.C. |
| 80 | 5 | H.S. | N.N. | N.C. | N.C. | N.C. | N.C. | N.C. | N.C. |
| | 25 | H.S. | N.N. | N.C. | N.C. | N.C. | N.C. | N.C. | N.C. |

S.G. = Slight Growth as needle
F.N. = Few needles

The procedure of Example 1 was repeated at an anhydrous ampicillin concentration of 5% w/v at both pH 5.0 and 6.5. The results are shown in Table II, a sucrose concentration of 80% w/v prevented hydrate formation at storage temperatures of both 5 and 25° C for 14 days. A sucrose concentration of 70% w/v prevented hydrate formation at 25° C., and retarded hydrate formation at 5° C. for 14 days. Similar results were obtained at both pH 5.0 and 6.5.

EXAMPLE 3

The procedure of Example 1 was repeated at an anhydrous ampicillin concentration of 10% w/v at both pH 5.0 and 6.5. The results are shown below in table III. As may be seen in Table III, a sucrose concentration of 80% w/v prevented hydrate formation at storage temperatures of both 5° and 25° C. for 14 days. A sucrose concentration of 70% w/v prevented hydrate formation at 25° C. and retarded hydrate formation at 5° C. for 14 days. Similar results were obtained at both pH 5.0 and 6.5.

Table III

| | | Ampicillin Concentration: 10% w/v (100 mg./ml) | | | | | | | |
|---|---|---|---|---|---|---|---|---|---|
| Sucrose Conc., % w/v | Storage Temp. °C | Initial | | After 3 Days | | After 7 Days | | After 14 Days | |
| | | Physical | Microscopic | Physical | Microscopic | Physical | Microscopic | Physical | Microscopic |
| None (Control) | 5 | H.S. | N.N. | Growth | N.L.G. | N.T. | N.T. | N.T. | N.T. |
| | 25 | H.S. | N.N. | Growth | N.L.G. | N.T. | N.T. | N.T. | N.T. |
| 50 | 5 | H.S. | N.N. | Growth | N.L.G. | N.T. | N.T. | N.T. | N.T. |
| | 25 | H.S. | N.N. | N.C. | N.C. | N.C. | N.C. | N.C. | N.C. |
| 60 | 5 | H.S. | N.N. | Some Growth | N.L.G. | Growth | N.L.G. | N.T. | N.T. |
| | 25 | H.S. | N.N. | N.C. | N.C. | N.C. | N.C. | N.C. | N.C. |
| 70 | 5 | H.S. | N.N. | N.C. | N.C. | S.G. | F.N. | S.G. | F.N. |
| | 25 | H.S. | N.N. | N.C. | N.C. | N.C. | N.C. | N.C. | N.C. |
| 80 | 5 | H.S. | N.N. | N.C. | N.C. | N.C. | N.C. | N.C. | N.C. |
| | 25 | H.S. | N.N. | N.C. | N.C. | N.C. | N.C. | N.C. | N.C. |

Based on the foregoing experiments, about 70% w/v sucrose concentrations are required to inhibit the crystal changes. Sucrose concentrations of about 60% w/v may be used at lower pH values below pH 5, but sucrose concentration about 80% w/v is required to stabilize a product at about pH 6.

An operative limit of about 80% w/v sucrose, or greater, is the preferred range to assure stabilization of ampicillin at a product pH of about 6 for storage under refrigerated conditions.

EXAMPLE 4

The procedure for Example 1 was repeated substituting dextrose or galactose for sucrose using the required concentration of these sugars (that is 0, 10, 20, 35, and 40% w/v, as necessary). Results of visual and microscopic examination for up to two weeks were recorded following storage at room temperature or refrigerated temperature conditions. The results for dextrose were the same as those for galactose. These are given in the following Table IV:

formation and physical changes at normal storage temperatures. At pH 5.0, 10–20% of these sugars will prevent growth at room temperature. However, at refrigerated temperatures, around 35% concentration is required at pH 6.0. At pH 5.0 at refrigerated temperatures, about 50% w/v dextrose prevents the hydration of ampicillin while up to 70% w/v galactose has no influence under these conditions.

EXAMPLE 5

The procedure of Example 1 was repeated substituting sodium chloride for the sucrose in the recipe as follows:

| Ingredient | Control | A | B | C | D |
|---|---|---|---|---|---|
| Anhydrous Ampicillin | 2.00 Gm. | 2.00 Gm. | 2.00 Gm. | 2.00 Gm. | 2.00 Gm. |
| Sodium Benzoate | 0.40 Gm. | 0.40 Gm. | 0.40 Gm. | 0.40 Gm. | 0.40 Gm. |
| Sodium Citrate | 0.16 Gm. | 0.16 Gm. | 0.16 Gm. | 0.16 Gm. | 0.16 Gm. |
| Propylparaben | 0.01 Gm. | 0.01 Gm. | 0.01 Gm. | 0.01 Gm. | 0.01 Gm. |
| Methylparaben | 0.09 Gm. | 0.09 Gm. | 0.09 Gm. | 0.09 Gm. | 0.09 Gm. |
| Sodium Chloride | — | 4.00 Gm. | 12.00 Gm. | 16.00 Gm. | 20.00 Gm. |
| NaCl Concentration | (0% w/v) | (5% w/v) | (15% w/v) | (20% w/v) | (25% w/v) |

More sodium citrate or citric acid was added to adjust the pH to the desired value. The results are shown below in Table V.

TABLE IV

Effect of Dextrose or Galactose

| Sample | pH | Storage Temp. °C | Initial Physical | Initial Microscopic | After 3 Days Physical | After 3 Days Microscopic | After 7 Days Physical | After 7 Days Microscopic | After 14 Days Physical | After 14 Days Microscopic |
|---|---|---|---|---|---|---|---|---|---|---|
| Control | 6.5 | 25 | H.S. | N.N. | Growth | N.L.G. | N.L.G. | N.L.G. | N.L.G. | N.L.G. |
| (10% w/v) | 6.5 | 25 or 5 | H.S. | N.N. | N.C. | N.C. | N.C. | N.C. | N.C. | N.C. |
| (40% w/v) | 6.5 | 25 or 5 | H.S. | N.N. | N.C. | N.C. | N.C. | N.C. | N.C. | N.C. |
| (10% w/v) | 5.0 | 25 | H.S. | N.N. | N.C. | N.C. | N.C. | N.C. | N.C. | Large number of needles |
| (20% w/v) | 5.0 | 25 | H.S. | N.N. | N.C. | N.C. | N.C. | N.C. | N.C. | N.C. |
| Control | 5.0 | 5 | H.S. | N.N. | Growth | N.L.G. | N.L.G. | N.L.G. | N.L.G. | N.L.G. |
| (20% w/v) | 5.0 | 5 | H.S. | N.N. | Growth | N.L.G. | N.L.G. | N.L.G. | N.L.G. | N.L.G. |
| (40% w/v) | 5.0 | 5 | H.S. | N.N. | Growth | N.L.G. | N.L.G. | N.L.G. | N.L.G. | N.L.G. |
| (25% w/v) | 6.0 | 25 or 5 | H.S. | N.N. | Growth | N.L.G. | N.L.G. | N.L.G. | N.L.G. | N.L.G. |
| (35% w/v) | 6.0 | 25 or 5 | H.S. | N.N. | N.C. | N.C. | N.C. | N.C. | N.C. | N.C. |

Results recorded in Table IV show that greater amounts of dextrose or galactose are required to prevent crystal growth and hydration of ampicillin as the pH is decreased from 6.5 to 6.0 or 5.0. Thus, at pH 6.5, about 10% dextrose or galactose will prevent hydrate

TABLE V

Effect of Sodium Chloride

| Sample | pH | Storage Temp. °C | Initial Physical | Initial Microscopic | After 3 Days Physical | After 3 Days Microscopic | After 7 Days Physical | After 7 Days Microscopic | After 14 Days Physical | After 14 Days Microscopic |
|---|---|---|---|---|---|---|---|---|---|---|
| Control | 6.5 | — | H.S. | N.N. | Growth | N.L.G. | N.T. | N.T. | N.T. | N.T. |
| A | 6.5 | 25 | H.S. | N.N. | N.C. | N.C. | N.C. | N.T. | N.C. | N.C. |
| A | 6.5 | 5 | H.S. | N.N. | Growth | N.L.G. | N.T. | N.T. | N.T. | N.T. |
| B | 6.5 | 5 | H.S. | N.N. | Growth | N.L.G. | N.T. | N.T. | N.T. | N.T. |
| C | 6.5 | 5 | H.S. | N.N. | N.C. | Some needles | N.C. | Some Needles | N.C. | Some Needles |
| D | 6.5 | 5 | H.S. | N.N. | N.C. | N.C. | N.C. | N.C. | N.C. | N.C. |
| Control | 5.0 | 25 | H.S. | N.N. | Growth | N.L.G. | N.T. | N.T. | N.T. | N.T. |
| A | 5.0 | 25 | H.S. | N.N. | N.C. | N.C. | N.C. | N.C. | N.C. | N.C. |
| A | 5.0 | 5 | H.S. | N.N. | Growth | N.L.G. | N.T. | N.T. | N.T. | N.T. |
| B | 5.0 | 5 | H.S. | N.N. | N.C. | Some needles | N.C. | Some needles | N.C. | Some needles |
| C | 5.0 | 5 | H.S. | N.N. | N.C. | N.C. | N.C. | N.C. | N.C. | N.C. |

The results recorded in Table V show that the pH has no influence on the effect of sodium chloride in preventing the hydration of ampicillin. About 5% w/v sodium chloride is required to prevent hydrate formation for at least two weeks at room temperature while about 25% w/v is required at refrigerated temperatures.

EXAMPLE 6

The following example illustrates the effects of pH on the stabilization of an anhydrous ampicillin aqueous suspension.

A dry powder is prepared from the following recipe:

| | |
|---|---|
| Anhydrous Ampicillin | 2.00 Gm. |
| Sodium Biphosphate | 0.05 Gm. |
| Methylparaben | 0.09 Gm. |
| Propylparaben | 0.01 Gm. |
| Sodium Cyclamate | 0.27 Gm. |
| Sucrose | 22.00 Gm. |
| Sucrose Concentration | (27.5% w/v) |

The dry powder was reconstituted by mixing with water to make 80 milliliters of a suspension (125 milligrams/5 milliliters) and was adjusted to a pH of 4.0 by means of citric acid.

Following the same procedures samples were prepared having a pH of 3.0, 3.7, 4.0, 4.5, 5.0, 5.2, 6.0, respectively, by using citric acid or sodium hydroxide to adjust the pH.

The samples were divided into two groups. One group was stored at room temperature (25° C ± 2° C). The second group was stored in a refrigerator at a temperature of 5° C ± 2° C.

After 7 days the samples were analyzed by Differential Thermal Analysis while physical and microscopic observations were recorded for up to 14 days. The results are shown below in Table VI.

Formulations having a pH of 4.5 or higher show crystal growth at refrigerated temperatures both physically and microscopically, and the differential analysis shows the presence of excessive amounts of hydrated drug. At room temperature, crystal changes and hydrate formation occur at pHs above 5.2.

Based on the foregoing, a pH of 5.2 or lower is required for storage of aqueous suspensions of anhydrous ampicillin at room temperature. A pH lower than 4.5 is required to prevent crystal growth and hydrate formation of drugs stored at refrigerated temperatures (2°–15° C). At the lowest pH 3.0 no crystal change was apparent, however, crystal changes were at pH 4.5. No changes were noted at pH 4.2.

Based on the foregoing experiments, a pH range of 5.2 to 3.0 are the limits for ampicillin solutions depending on storage temperatures.

Summarizing the foregoing, the objects of the invention may be achieved with a stabilized aqueous pharmaceutical suspension comprising A. 1.25 to 10 percent by weight per volume of anhydrous ampicillin;

B. A member selected from the class consisting of a minimum range of 10 to 50% w/v dextrose, a minimum range of 10 to 35% w/v galactose and a minimum range of 5 to 25% w/v sodium chloride; and C. A buffer adjusting the pH to a range between about 5 to 6.5, where the lowest end of the minimum range of solutes is used at pH 6.5 at 25° C and the highest end of the minimum range of solutes is used at pH 5 at 5° C, with the proviso that galactose is not effective below pH 6.0 at 5° C.

The terms and expressions which have been employed are used as terms of description and not of

TABLE VI

Effect of pH in Presence of 27.5% w/v Sucrose

| pH of Sample | Storage Temp. ° C. | Initial Physical | Initial Microscopic | After 7 Days Physical | After 7 Days Microscopic | After 7 Days DTA | After 14 Days Physical | After 14 Days Microscopic |
|---|---|---|---|---|---|---|---|---|
| 6.0 | 25 | H.S. | N.N. | Growth | N.L.G. | >10% | Growth | N.L.G. |
| 5.5 | 25 | H.S. | N.N. | Growth | N.L.G. | >10% | Growth | N.L.G. |
| 5.35 | 25 | H.S. | N.N. | Growth | N.L.G. | 10–20% None | Growth | N.L.G. |
| 5.2 or 5.0 | 25 | H.S. | N.N. | N.C. | Very few needles | Detected (<10%) None | N.C. | Very few needles |
| 4.0 or 4.5 | 25 | H.S. | N.N. | N.C. | N.C. | Detected (<10%) | N.C. | N.C. |
| 6.0, 5.5 or 5.0 | 5 | H.S. | N.N. | Growth | N.L.G. | N.T. | Growth | N.L.G. |
| 4.5 | 5 | H.S. | N.N. | Growth | N.L.G. | >20% None | Growth | N.L.G. |
| 4.0 | 5 | H.S. | N.N. | N.C. | N.C. | Detected (<10%) None | N.C. | N.C. |
| 3.7 | 5 | H.S. | N.N. | N.C. | N.C. | Detected (<10%) | N.C. | N.C. |
| 3.0 | 5 | H.S. | N.N. | N.C. | N.C. | N.T. | N.C. | N.C. |

Table VI shows that good agreement exists between microscopic observations and DTA results. The following conclusions may be drawn from Table VI.

The pH 4.0 sample does not show any crystal growth, physically or microscopically for a least two weeks. Same sample stored for over one month did not show any growth. No hydrate is detected by Differential Thermal Analysis after storage of the suspension at room temperature and refrigerated conditions for two weeks. Similar results are obtained at pH values below pH 4.3.

limitation, and there is no intention in the use of such terms and expressions of excluding any equivalents of the features shown and described or portions thereof, but it is recognized that various modifications are possible within the scope of the invention claimed.

For instance as will appear from the foregoing, various modifications of the foregoing, employing the invention are possible within the scope thereof as defined by the appended claims so long as the advantages of the invention with respect to conversion to hydrated forms and physical stability are attained. In addition it should be noted that the variations given above and in the claims are those tested in laboratories.

What is claimed is:

1. A stabilized aqueous pharmaceutical suspension comprising:
    A. 1.25 to 10 percent by weight per volume of anhydrous ampicillin;
    B. A member selected from the class consisting of a minimum range of 10–50% w/v dextrose, a minimum range of 10–35% w/v galactose, and a minimum range of 5–25% w/v sodium chloride; and
    C. A buffer adjusting the pH to a range between about 5 to 6.5, wherein said lowest minimum range of solutes is used at pH 6.5 at 25° C and said highest minimum range of solute is used at pH 5 at about 5° C with the proviso that galactose is not effective below pH 6.0 at 5° C.

2. A stabilized aqueous pharmaceutical suspension as defined in claim 1 comprising:
    A. 2.5 to 10% w/v of anyhydrous ampicillin;
    B. A minimum range of 10–50% w/v dextrose and
    C. A buffer adjusting the pH to a range between about 5.0 to 6.5.

3. A stabilized aqueous pharmaceutical composition as defined in claim 1 comprising:
    A. 2.5 to 10% w/v of anhydrous ampicillin; and
    B. A minimum range of 5 to 25% w/v of sodium chloride 4. A stabilized aqueous pharmaceutical composition for storage at 5°–25° C. as defined in claim 1 comprising:
    A. 2.5 to 10% w/v of anhydrous ampicillin;
    B. A minimum range of 10–35% w/v galactose; and
    C. A buffer adjusting the pH to a range between about 5.0 to 6.5.

* * * * *

UNITED STATES PATENT AND TRADEMARK OFFICE
CERTIFICATE OF CORRECTION

PATENT NO. : 3,993,753
DATED : November 23, 1976
INVENTOR(S) : Surendra M. Bahal It is certified that error appears in the above-identified patent and that said Letters Patent are hereby corrected as shown below:

In Table I-A the symbol $>$ in column headed "Microscopic" should appear adjacent the term 20% in column headed "DTA" to read as follows: $>20\%$ Signed and Sealed this Fifth Day of April 1977

[SEAL]

Attest:

RUTH C. MASON
*Attesting Officer*

C. MARSHALL DANN
*Commissioner of Patents and Trademarks*